United States Patent
Wang et al.

(10) Patent No.: US 10,648,037 B2
(45) Date of Patent: May 12, 2020

(54) METHOD AND KIT FOR NON-INVASIVELY DETECTING EGFR GENE MUTATIONS

(71) Applicant: BERRY GENOMICS CO., LTD, Beijing (CN)

(72) Inventors: Lina Wang, Beijing (CN); Lanlan Ru, Beijing (CN); Tiancheng Li, Beijing (CN); Yaxi Zhang, Beijing (CN); Jianguang Zhang, Beijing (CN)

(73) Assignee: Berry Genomics Co., Ltd., Beijing (CN)

( * ) Notice: Subject to any disclaimer, the term of this patent is extended or adjusted under 35 U.S.C. 154(b) by 663 days.

(21) Appl. No.: 15/109,308

(22) PCT Filed: Dec. 16, 2014

(86) PCT No.: PCT/CN2014/093940
§ 371 (c)(1),
(2) Date: Jun. 30, 2016

(87) PCT Pub. No.: WO2015/101175
PCT Pub. Date: Jul. 9, 2015

(65) Prior Publication Data
US 2017/0009302 A1    Jan. 12, 2017

(30) Foreign Application Priority Data

Dec. 31, 2013  (CN) .......................... 2013 1 0756037

(51) Int. Cl.
*C12Q 1/6886*    (2018.01)
*C12Q 1/6853*    (2018.01)

(52) U.S. Cl.
CPC ......... *C12Q 1/6886* (2013.01); *C12Q 1/6853* (2013.01); *C12Q 2600/156* (2013.01); *C12Q 2600/16* (2013.01)

(58) Field of Classification Search
None
See application file for complete search history.

(56) References Cited

U.S. PATENT DOCUMENTS 6,312,913 B1 *  11/2001  Wang ................... C12Q 1/6855
                                              435/6.11
2012/0270212 A1 *  10/2012  Rabinowitz .......... C12Q 1/6862
                                              435/6.11

(Continued)

FOREIGN PATENT DOCUMENTS

| CN | 101967684 A | 2/2011 |
| CN | 103298955 A | 9/2013 |
| WO | WO-2013/138510 A1 | 9/2013 |

OTHER PUBLICATIONS

Myllykangas et al., "Targeted sequencing library preparation by genomic DNA circularization," BMC Biotechnology, vol. 11, No. 122, pp. 1-12. (Year: 2011).*

(Continued)

*Primary Examiner* — Young J Kim
(74) *Attorney, Agent, or Firm* — Womble Bond Dickinson (US) LLP; Cristin H. Cowles; Sai Seetharaman (57) ABSTRACT

The present invention discloses a method for non-invasively detecting EGFR gene mutations in subjects, comprising the following steps: designing primers according to EGFR gene exons; extracting plasma DNAs in subjects; connecting the extracted plasma DNAs with tagging linkers; PCR pre-amplifying the tagging linkers connected plasma DNAs; cyclising the pre-amplified DNAs to obtain cyclised DNAs; PCR amplifying the cyclised DNAs using the designed primers; and high throughput sequencing the PCR amplified product and analyzing the EGFR gene mutations. The present invention also discloses a corresponding kit.

4 Claims, 5 Drawing Sheets
Specification includes a Sequence Listing.

Design principle of the present invention

(56) References Cited

U.S. PATENT DOCUMENTS

2013/0309724 A1 11/2013 Candau-Cachon
2014/0228256 A1 8/2014 Zhang et al.
2015/0344964 A1* 12/2015 Hofler .................. C12Q 1/6886
                                                                    506/9

OTHER PUBLICATIONS

Angulo et al., "A Comparison of EGFR Mutation Testing Methods in Lung Carcinoma: Direct Sequencing, Real-time PCR and Immunohistochemistry," PLOS One, August, vol. 7, issue 8, e43842, pp. 1-12. (Year: 2012).*

Forshew et al., "Noninvasive Identification and Monitoring of Cancer Mutations by Targeted Deep Sequencing of Plasma DNA," Science Translation Medicine, May, vol. 4, No. 136, pp. 1-12 (Year: 2012).*

International Preliminary Report on Patentability dated Jul. 5, 2016 of International Application No. PCT/CN2014/093940.

Written Opinion of the International Searching Authority dated Mar. 20, 2015 of International Application No. PCT/CN2014/093940.

International Search Report dated Mar. 24, 2015 of International Application No. PCT/CN2014/093940.

Gregory, et al., "Targeted single molecule mutation detection with massively parallel sequencing," Nucleic Acids Research, Sep. 17, 2015, total 11 pages.

Supplementary European Search Report for EP Application No. 14877282.5 dated Jun. 2, 2017, total 8 pages.

Shore et al., "DNA Flexibility Studied by Covalent Closure of Short Fragments into Circles"; Department of Biochemistry, Stanford University School of Medicine; vol. 78, No. 8; pp. 4833-4837; Aug. 1981.

Czapla et al., "Sequence-Dependent Effects in the Cyclization of Short DNA"; Journal of Chemical Theory and Computation; No. 2; pp. 685-695; Jan. 17, 2006.

* cited by examiner

1 : PCR product before cyclization

2 : Product after cyclization (not digested by an exonuclease) M: marker 3 : Exonuclease digested product after cyclization (not purified)

4 : Exonuclease digested and purified product after cyclization

Cyclization rate of the present invention (6% denaturing gel)

Fig.3

Final library of EGFR sample (2% agarose gel)

Fig.4

1: LC2; 2: LC3; 3: LC113; 4: LC314; 5: LC320; 6: negative control;

M: 100bp DNA ladder (TaKaRa).

METHOD AND KIT FOR NON-INVASIVELY DETECTING EGFR GENE MUTATIONS

CROSS-REFERENCE TO RELATED APPLICATIONS

This application is a 35 U.S.C. § 371 national stage filing of International Application No. PCT/CN2014/093940, filed on Dec. 16, 2014, which claims the benefit of Chinese Patent Application No. 201310756037.2, filed on Dec. 31, 2013. The entire contents of each of the aforementioned applications are hereby incorporated by reference in their entirety.

SEQUENCE LISTING

The instant application contains a Sequence Listing which has been submitted in ASCII format via EFS-Web and is hereby incorporated by reference in its entirety. Said ASCII copy, created on Jun. 30, 2016, is named 118216_15201_ST25.txt and is 5,028 bytes in size.

FIELD OF INVENTION

The present invention relates to genetic diagnosis field. More specifically, the present invention is directed to a method for detecting Epidermal Growth Factor Receptor (EGFR) gene mutations, as well as a kit for use in the detection of EGFR gene mutations.

BACKGROUND OF INVENTION

EGFR (Epidermal Growth Factor Receptor) is normally embedded in the cell membrane on the cell surface. EGFR gene is 118 kb in length, includes 28 exons, and encodes a 170 kD glycoprotein comprised of 1186 amino acids. It is a membrane protein that plays an important role in regulating proliferation, growth, repair and survival of tumor cells. Currently, targeted therapy has become an important tool in the clinical treatment of Non Small Cell Lung Cancer (NSCLC). Iressa (Gefitinib, AstraZeneca) and Tarceva (Erlotinib, Roche), which function as EGFR tyrosine kinase inhibitors (TKI), are the main drugs approved by FDA for NSCLC targeted therapy. However, clinical experiments showed that Iressa and Tarceva only had significant therapeutic effects on 10-30% NSCLC patients. Further studies indicated that EGFR gene mutations relate to the therapeutic effects of NSCLC targeted therapy, and most of the patients carrying EGFR gene mutations showed significant therapeutic effects. A large number of research documents indicated that EGFR gene mutations are mainly located in the tyrosine kinase coding domain (exons 18-21), wherein deletion in exon 19 (746-753) accounts for about 45% of all mutations, and substitution in exon 21 (mainly L858R) accounts for about 40% of all mutations. At present, it is generally believed that these two hot mutations can enhance the sensitivity of tumor cells against TKI, and can be used as an effective index to predict TKI treatment. Therefore, the detection of EGFR gene mutations has an important reference value for guiding clinical administration in patients with NSCLC. Methods for detecting EGFR currently used in clinical treatment include: 1) traditional sequencing. This method has high accuracy. However, high requirement on the sample source, long sequencing time, the need for sequence analysis, and high cost of this method limit its use in clinic. 2) Polymerase chain reaction-single strand conformation polymorphism (PCR-SSCP). It is a classical method for detecting gene mutations, and can detect unknown mutations. It has advantages of simple operation and high sensitivity. However, it also has an obvious disadvantage, which is the requirement for parallel standard control. Additionally, this method has a high false positive: the detection rate is 75-95% when the tested PCR product is less than 200 bp, while the detection rate is only about 50% when the tested PCR sample is more than 400 bp. 3) Mutation enriched PCR: a two-step PCR using a restriction endonuclease to selectively digest the wild type EGFR gene. After the first PCR, the wild type EGFR is digested selectively and the mutated EGFR genes are enriched, and then the second PCR is conducted. The PCR product is detected by electrophoresis, and whether EGFR is mutated is determined based on the detection results of PCR product. This method is highly sensitive, and can detect one mutation among $10^3$-$10^4$ wild type EGFRs. However, this method needs twice PCR and enzyme digestion, thus is complex and time-consuming. In addition, there are technologies like AMRS and micro digital PCR, but their application in clinic still needs time.

Thus, there is an urgent need for a fast and efficient method for detecting EGFR gene mutations clinically. The inventor found, during the research of fragment DNA detection, a new method for detecting DNA fragments, including cyclizing and then amplifying DNA fragments. Based on this discovery and in combination with the second generation high throughput sequencing technology, the inventor improved the aforementioned method and designed optimized primers specifically based on the EGFR genes, and developed a method and a kit thereof for sequencing and analyzing EGFR gene mutations in plasma DNAs.

SUMMARY OF INVENTION

In one aspect, the present invention provides a method for non-invasively detecting EGFR gene mutations in subjects, comprising the following steps:
designing primers according to EGFR gene exons;
extracting plasma DNAs from the subjects;
connecting the extracted plasma DNAs with tagging linkers;
PCR pre-amplifying the tagging linkers connected plasma DNAs;
cyclizing the amplified DNAs to obtain cyclised DNAs;
PCR amplifying the cyclised DNAs using the designed primers; and
high throughput sequencing the PCR amplified product and analyzing the EGFR gene mutations.

Further, the primers are a pair of primers that are adjacent and backward extended.

Further, primers of the backward extended primer pair are located on 5' or 3' end of the EGFR gene exons.

Further, space of the backward extended primer pair is 0-½ of the total base pairs of the fragment DNAs.

Further, the backward extended primers aim at exon 18, exon 19, exon 20, or exon 21 of the EGFR genes.

Further, 5' end of the backward extended primers contains linker sequences for high throughput sequencing library.

Further, the backward extended primers aim at exon 18, exon 19, exon 20, or exon 21 of the EGFR genes, and sequences of the primers are as follows:

| | | |
|---|---|---|
| E18-1-3F: | CCCAGCTTGTGGAGCCTC | [SEQ ID NO.: 1] |
| E18-1-3R: | GACAAGAACACAGAGACAAGGGT | [SEQ ID NO.: 2] |
| E18-2-F: | GCAGGGCCTCTCATGGTC | [SEQ ID NO.: 3] |
| E18-2-R: | CCTGTGCCAGGGACCTTAC | [SEQ ID NO.: 4] |
| E19-1-F: | ACGTCTTCCTTCTCTCTCTGTCAT | [SEQ ID NO.: 5] |
| E19-1-R: | GTGAGATGGTGCCACATGCT | [SEQ ID NO.: 6] |

```
E19-2-F:   GTCCATGGCTCTGAACCTCA       [SEQ ID NO.: 7]
E19-2-R:   CCACACAGCAAAGCAGAAAC       [SEQ ID NO.: 8]
E20-1-F:   CACACTGACGTGCCTCTCC        [SEQ ID NO.: 9]
E20-1-R:   CTTCGCATGGTGGCCAGA         [SEQ ID NO.: 10]
E20-2-1F:  CCTCCCCGTATCTCCCT          [SEQ ID NO.: 11]
E20-2-1R:  GGAGATAAGGAGCCAGGAT        [SEQ ID NO.: 12]
E21-1-F:   AGCAGGGTCTTCTCTGTTTCA      [SEQ ID NO.: 13]
E21-1-R:   GAGGGACAGATCATCATGGG       [SEQ ID NO.: 14]
E21-2-F:   TTTCCTGACACCAGGGACC        [SEQ ID NO.: 15]
E21-2-R:   TGACCTAAAGCCACCTCCTT.      [SEQ ID NO.: 16]
```

Further, the cyclization is a splint mediated single strand DNA cyclization.

Further, the EGFR genes in plasma DNAs have insertion, deletion, substitution or gene fusion mutations.

Further, the high throughput sequencing technologies are selected from Roche/454 FLX, Illumina/Hiseq/Miseq, Applied Biosystems SOLID and life Technologies/Ion Torrent/Proton.

In another aspect, the present invention provides a kit for non-invasively detecting EGFR gene mutations, comprising: reagents for extracting plasma DNAs, a DNA cyclase, primers and reagents for amplifying target DNAs.

Further, the kit comprises primers and reagents for pre-amplifying regions to be tested in the EGFR genes.

Further, the kit comprises reagents for high throughput sequencing.

Further, the reagents for high throughput sequencing are applicable to the following high throughput sequencing technologies: Roche/454 FLX, Illumina/Hiseq/Miseq, Applied Biosystems SOLID and life Technologies/Ion Torrent/Proton.

Further, the primers for amplifying regions to be tested in the EGFR genes are a pair of primers that are adjacent and backward extended.

Further, primers of the backward extended primer pair are located on 5' or 3' end of the sites or regions to be tested in the EGFR genes.

Further, space of the backward extended primer pair is 0-½ of total base pairs of the plasma DNAs.

Further, the backward extended primers aim at exon 18, exon 19, exon 20, or exon 21 of the EGFR genes.

Further, the backward extended primers aim at exon 18, exon 19, exon 20, or exon 21 of the EGFR genes, and sequences of the primers are as follows:

```
E18-1-3F:  CCCAGCTTGTGGAGCCTC         [SEQ ID NO.: 1]
E18-1-3R:  GACAAGAACACAGAGACAAGGGT    [SEQ ID NO.: 2]
E18-2-F:   GCAGGGCCTCTCATGGTC         [SEQ ID NO.: 3]
E18-2-R:   CCTGTGCCAGGGACCTTAC        [SEQ ID NO.: 4]
E19-1-F:   ACGTCTTCCTTCTCTCTCTGTCAT   [SEQ ID NO.: 5]
E19-1-R:   GTGAGATGGTGCCACATGCT       [SEQ ID NO.: 6]
E19-2-F:   GTCCATGGCTCTGAACCTCA       [SEQ ID NO.: 7]
E19-2-R:   CCACACAGCAAAGCAGAAAC       [SEQ ID NO.: 8]
E20-1-F:   CACACTGACGTGCCTCTCC        [SEQ ID NO.: 9]
E20-1-R:   CTTCGCATGGTGGCCAGA         [SEQ ID NO.: 10]
E20-2-1F:  CCTCCCCGTATCTCCCT          [SEQ ID NO.: 11]
E20-2-1R:  GGAGATAAGGAGCCAGGAT        [SEQ ID NO.: 12]
E21-1-F:   AGCAGGGTCTTCTCTGTTTCA      [SEQ ID NO.: 13]
E21-1-R:   GAGGGACAGATCATCATGGG       [SEQ ID NO.: 14]
E21-2-F:   TTTCCTGACACCAGGGACC        [SEQ ID NO.: 15]
E21-2-R:   TGACCTAAAGCCACCTCCTT.      [SEQ ID NO.: 16]
```

Further, the plasma DNA linkers contain tagging sequences.

Further, the plasma DNAs are pre-amplified before they are cyclised.

Further, the cyclization is a splint mediated single strand DNA cyclization.

Further, the sites or regions to be tested in the EGFR genes have insertion, deletion, substitution or gene fusion mutations.

In yet another aspect, the present invention provides a use of primers against EGFR gene exons in the preparation of diagnosing reagents or kits for non-invasively detecting EGFR gene mutations in subjects, characterized in that the diagnosing reagents or kits are applicable to a method for non-invasively detecting EGFR gene mutations in subjects comprising the following steps:

extracting plasma DNAs from the subjects;
connecting the extracted plasma DNAs with tagging linkers;
PCR pre-amplifying the tagging linkers connected plasma DNAs;
cyclizing the amplified DNAs to obtain cyclised DNAs;
PCR amplifying the cyclised DNAs using the designed primers; and
high throughput sequencing the PCR amplified product and analyzing the EGFR gene mutations.

Further, the primers are a pair of primers that are adjacent and backward extended.

Further, primers of the backward extended primer pair are located on 5' or 3' end of the EGFR gene exons.

Further, space of the backward extended primer pair is 0-½ of total base pairs of the fragment DNAs.

Further, the backward extended primers aim at exon 18, exon 19, exon 20, or exon 21 of the EGFR genes.

Further, 5' end of the backward extended primers contains linker sequences for high throughput sequencing library.

Further, the backward extended primers aim at exon 18, exon 19, exon 20, or exon 21 of the EGFR genes, and sequences of the primers are as follows:

```
E18-1-3F:  CCCAGCTTGTGGAGCCTC         [SEQ ID NO.: 1]
E18-1-3R:  GACAAGAACACAGAGACAAGGGT    [SEQ ID NO.: 2]
E18-2-F:   GCAGGGCCTCTCATGGTC         [SEQ ID NO.: 3]
E18-2-R:   CCTGTGCCAGGGACCTTAC        [SEQ ID NO.: 4]
E19-1-F:   ACGTCTTCCTTCTCTCTCTGTCAT   [SEQ ID NO.: 5]
E19-1-R:   GTGAGATGGTGCCACATGCT       [SEQ ID NO.: 6]
E19-2-F:   GTCCATGGCTCTGAACCTCA       [SEQ ID NO.: 7]
E19-2-R:   CCACACAGCAAAGCAGAAAC       [SEQ ID NO.: 8]
E20-1-F:   CACACTGACGTGCCTCTCC        [SEQ ID NO.: 9]
E20-1-R:   CTTCGCATGGTGGCCAGA         [SEQ ID NO.: 10]
E20-2-1F:  CCTCCCCGTATCTCCCT          [SEQ ID NO.: 11]
E20-2-1R:  GGAGATAAGGAGCCAGGAT        [SEQ ID NO.: 12]
E21-1-F:   AGCAGGGTCTTCTCTGTTTCA      [SEQ ID NO.: 13]
E21-1-R:   GAGGGACAGATCATCATGGG       [SEQ ID NO.: 14]
E21-2-F:   TTTCCTGACACCAGGGACC        [SEQ ID NO.: 15]
E21-2-R:   TGACCTAAAGCCACCTCCTT.      [SEQ ID NO.: 16]
```

Further, the cyclization is a splint mediated single strand DNA cyclization.

Further, the EGFR genes in the plasma DNAs have insertion, deletion, substitution or gene fusion mutations.

Further, the high throughput sequencing is selected from Roche/454 FLX, Illumina/Hiseq/Miseq, Applied Biosystems SOLID and life Technologies/Ion Torrent/Proton.

BRIEF DESCRIPTION OF FIGURES

FIG. 1 shows experimental design of the present invention. The plasma DNA is first pre-amplified to increase yield of the detection product, and then the pre-amplified DNA is cyclised to increase available templates for detection. The EGFR gene is amplified to prepare a library for high throughput sequencing.

FIG. 2 shows design principle of the cyclization of the present invention. The pre-amplified DNA is a double strand DNA with universal linkers on both ends. Splint with reverse complimentary sequences is designed based on the sequences of the universal linkers on both ends, and a partial double strand is formed after annealing and hybridization. Single strand cyclised product is finally obtained by ligation using Tap ligase.

FIG. 3 shows cyclization rate of the present invention. This figure shows the imaging results of 6% denaturing gel. 1: a PCR product before cyclization; 2: a product after cyclization (not digested by exonuclease), M: a marker; 3: an exonuclease digested product after cyclization (not purified); 4: an exonuclease digested and purified product after cyclization.

EMBODIMENTS

With improvements in the sequencing technology, the traditional Sanger sequencing has been unable to fully meet the requirement of research. Thus, the second generation sequencing technology with lower cost, higher throughput, faster speed, and having capability for sequencing the whole genome emerges. The main principle of the second generation sequencing technology is high throughput sequencing by synthesis, namely, determining DNA sequences by capturing newly synthesized end labelling. The available technologic platforms mainly include Roche/454 FLX, Illumina/Genome Analyzer/Hiseq/Miseq, Applied Biosystems SOLID, life Technologies/Ion Torrent, and the like. Taking Illumina product as an example, HiSeq 2000 can reach a sequencing throughput of 30× coverage in 6 human genomes per run, i.e., about 600 G/run, and the operation time is reduced to 30 minutes. Furthermore, with the maturity of the second generation sequencing technology, the investigation on its clinical application has developed quickly. Research shows that fetus genetic health can be judged by sequencing maternal plasma DNAs, and that sequencing plasma DNAs in subjects can be used for early cancer screening, which will have a wide application in the future.

Plasma DNAs, also known as circulating DNAs, are extracellular DNAs in the blood and is tens to hundreds of nucleotides in length (a main peak of about 167 bp). It presents in a form of DNA-protein complex, or as free DNA fragments. Normally, plasma DNAs are derived from DNA release of a small amount of senescent and dead cells. Under healthy condition, the generation and removal of the circulating DNAs are in a dynamic equilibrium and are maintained at a relatively steady low level. 1 mL plasma from a normal person contains about 2000 genomic DNAs. The circulating DNAs can reflect the metabolic condition of cells in human body, thus is an important index for judging health. The change of quantity and quality of circulating DNAs in peripheral blood is closely related to several diseases (including tumour, complex severe traumata, organ transplantation, pregnancy-related diseases, infectious diseases, organ failure, and the like). As a non-invasive detection index, it is expected to be an important molecular marker for early diagnosing some diseases, monitoring the conditions, and evaluating the therapeutic effects and prognosis of the diseases. For example, researches show that EGFR regulates the cell cycle progress, repair and survival of tumor cells, and at the same time relates to tumor metastasis. Recently, molecular targeted therapy using EGFR as the therapy target has received widespread attention from cancer communities both at home and abroad, and an EGFR tyrosine kinase inhibitor, Iressa (Genfitinib), has been approved by America Food and Drug Administration (FDA) for treating advanced NSCLC. The prominent feature of molecular targeted drugs is that its therapeutic effect strongly depends on the target: the therapeutic effect is significant strong in patients with the "target", while the therapeutic effect is weak or none in patients without the "target", which thus delays other treatments and makes the conditions worse. Therefore, blind administrations without target detection not only may result in high economic loss, but also may delay the valuable timing for treatment, or even aggravate the conditions. It is curtail to judge quickly and accurately whether the patient has the specific target for the targeted drug treatment. The traditional EGFR detection mainly detects the lesion tissue section by FISHor qPCR. However, it is found that there are more free DNAs in the plasma of NSCLC patients, about 10 times of those of normal people. A large quantity of free DNAs in plasma derives from DNAs release of senescent and dead tumor cells. They are similar to tumor genomic DNAs in genetic characteristics, and mutations thereof include deletion, point mutation, and increased copy number. EGFR gene mutations can be detected by examining plasma DNAs in NSCLC patients, and thus make it possible to detect EGFR expression non-invasively. The present invention detects EGFR expressions and mutations in plasma DNAs by the second generation sequencing technology quickly, accurately, non-invasively and with high sensitivity, and thus provides various diagnosis basis for patients.

In view of the clinical significance of non-invasive detection by plasma DNAs sequencing and the rapid development of the second generation high throughput sequencing, the inventor found that sequencing plasma DNAs in large-scale can detect EGFR gene expressions and mutations more quickly, accurately, and non-invasively. It is applicable to a variety of second generation high throughput sequencing platforms, including but not limited to, Roche/454 FLX, Illumina/Genome Analyzer/Hiseq/Miseq, Applied Biosystems SOLID, life Technologies/Ion Torrent, and the like.

The present invention is based on the following two facts: 1) plasma free DNAs in patients are similar to genomic DNAs in genetic characteristics. The plasma free DNAs of patients are higher in content than those of normal people, and often contain lots of mutations, while each mutation may be of low frequency; 2) The second generation high throughput sequencing can obtain the information of plasma free DNAs quickly, accurately, and with high throughput. Combining these two facts enables the non-invasive large scale application of the detection in genome specific regions. Researches show that plasma DNAs exist as fragments with low amount (1 mL plasma contains about 2000 genomes) and short length (mainly about 167 bp), which make it difficult for the traditional PCR to enrich mutations effectively using plasma DNAs as templates, resulting in rapid decrease in detection sensitivity. The present invention differs from the traditional methods in that the DNA fragments connected with sequence tagging linkers are amplified and single strand cyclized, then by means of back-to-back primer amplification, the templates are used maximally and the library is sequenced by high throughput paired-end sequencing. The original amplified templates are assembled based on the original sequencing analysis, and the tagging sequences are recorded. Sequences with the same position on the genome and the same tagging sequences are calculated as one template. The number of templates amplified by every primer pair is calculated and the number of mutated template is counted and recorded. The present invention improves the cyclization method and optimizes primers for the EGFR genes. The unique design of tagging sequences reduces background and prevents contamination effectively. The unique template set is counted by restoring templates in systems accurately, and thus a single molecule detection with high accuracy is finally achieved.

Figure 1:
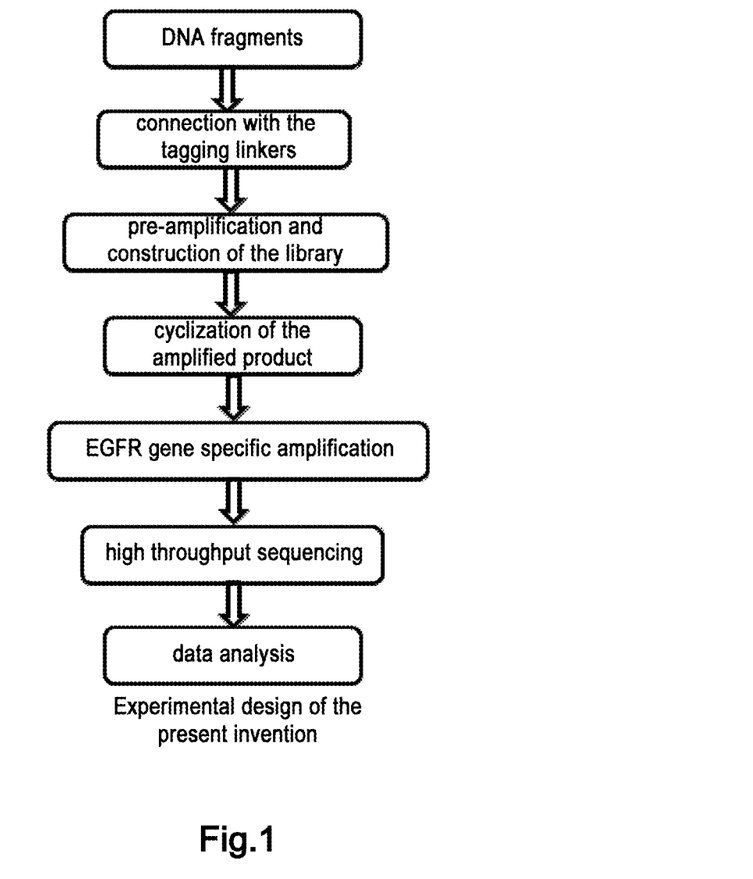
Figure 2A:
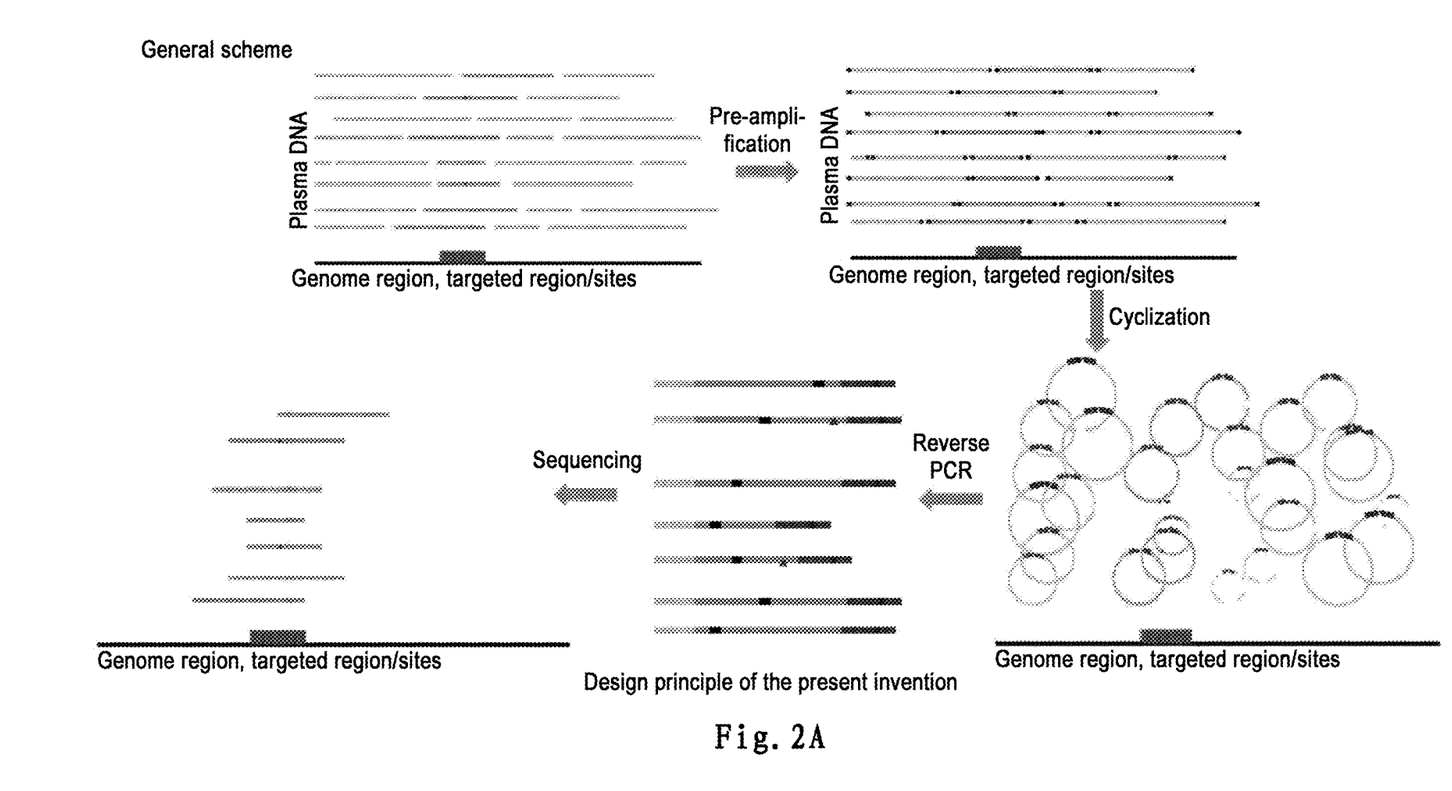
FIG. 2A shows a general scheme.
Figure 2B:
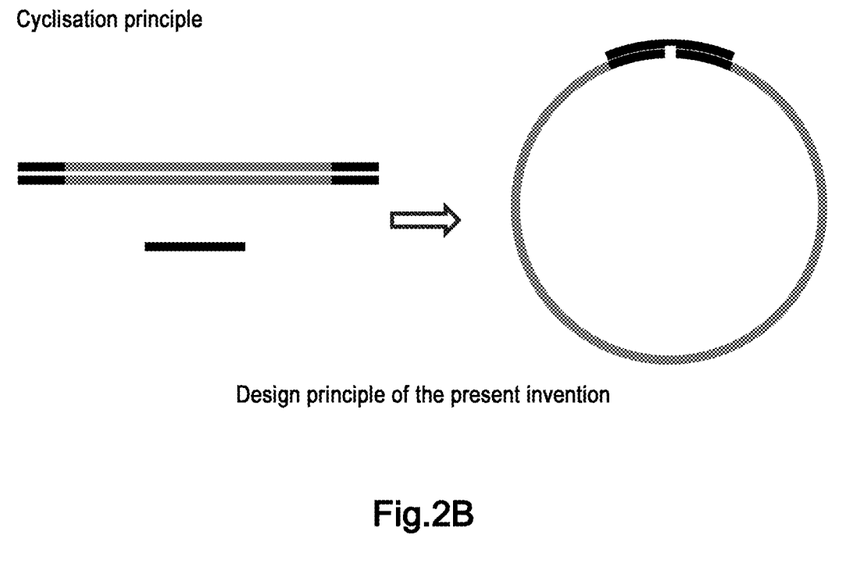
FIG. 2B shows the cyclization principle.

According to one specific embodiment of the present invention, it provides a method for non-invasively detecting EGFR gene mutations in subjects, comprising the following steps: (1) designing primers according to EGFR gene exons; (2) extracting plasma DNAs from the subjects; (3) connecting the extracted plasma DNAs with tagging linkers; (4) PCR pre-amplifying the tagging linkers connected plasma DNA; (5) cyclizing the amplified DNAs to obtain cyclised DNAs; (6) PCR amplifying the cyclised DNAs using the designed primers; and (7) high throughput sequencing the PCR amplified product and analyzing the EGFR gene mutations. "Non-invasive detection" in the present invention means that in comparison with that routine histology detection methods such as surgery, tissue biopsy and the like, which are directly against cancer tissues, will result in body damages in subjects, the present invention only detects blood sample from the subjects. Traditional methods for detecting DNAs or gene fragments require PCR amplification of the regions to be tested before detection, and thus the DNAs or gene fragments to be tested should be complete. However, most of the plasma DNA fragments are incomplete, and thus the DNA fragments that can be used as templates in PCR amplification is few in number and is difficult to be detected by a routine PCR. Therefore, PCR amplification in the present invention adopts DNA cycllization technology to transform fragment DNAs into cyclic DNAs using linker sequences and enzymes. Primers based on the regions to be tested are designed; sequencing library is amplified and constructed, and then is sequenced by a high throughput sequencing technology; and the EGFR gene mutations are analyzed. FIG. 1 shows principle of the present invention. Plasma DNA is first extracted and connected with tagging linkers, which is in Y-shape. The double strand region contains tagging sequences that are distinguishable between different templates. To increase the amount of amplificable DNA fragments, pre-amplification can be conducted, universal sequence on the primers and linkers can be annealed, and then the pre-amplified DNAs are cyclised, for example, using a splint. FIG. 2 shows DNA cyclization principle of the present invention. Splint sequence and the pre-amplified primer region are complementary. Primers according to EGFR exons, for example, exon 18, 19, 20 and 21, are designed, and specific PCR amplification according to EGFR genes is conducted to generate a sequencing library, which is then sequenced by the current high throughput sequencing technology to obtain the specific regions in the tested EGFR genes, namely, gene sequences of the exons, and then gene mutations in the specific region are analyzed. The high throughput sequencing of the present invention refers to the available second generation sequencing techonology, such as Roche/454 FLX, Illumina/Genome Analyzer/Hiseq/Miseq, Applied Biosystems SOLID, life Technologies/Ion Torrent and the like. Different platforms differ in sequencing principles. Taking IlluminaMiseq as an example, the generated sequencing library is denatured and high throughput sequenced in a Miseq sequencer. The read length is 250 bp on both ends, and every primer site produces about 100, 000 sequences. The double-end sequences are combined to a single end sequence based on terminal repeated regions. Linker regions in the single end sequence are searched, and the sequence is restored to the original plasma DNA fragments, while the tagging sequence in every sequence is recorded. The restored DNA fragments are compared with human genome, with the start and terminal coordinates of the sequence on the genome recorded. A unique template sequence is obtained after redundancy removal using the start and terminal coordinates and tagging sequences as standards. The type and ratio of mutations are determined by counting the template sequences in the target zone.

According to another further specific embodiment of the present invention, primers of the backward extended primer pair are located on 5' or 3' end of the EGFR gene exons. Further, space of the backward extended primer pair is 0-½ of total base pairs of the fragment DNAs. Further, the backward extended primers aim at exon 18, exon 19, exon 20, or exon 21 of the EGFR genes. Further, 5' end of the backward extended primers contains linker sequences for high throughput sequencing library. Further, the backward extended primers aim at exon 18, exon 19, exon 20, or exon 21 of EGFR genes, and sequences of the primers are as follows:

| | | |
|---|---|---|
| E18-1-3F: | CCCAGCTTGTGGAGCCTC | [SEQ ID NO.: 1] |
| E18-1-3R: | GACAAGAACACAGAGACAAGGGT | [SEQ ID NO.: 2] |
| E18-2-F: | GCAGGGCCTCTCATGGTC | [SEQ ID NO.: 3] |
| E18-2-R: | CCTGTGCCAGGGACCTTAC | [SEQ ID NO.: 4] |
| E19-1-F: | ACGTCTTCCTTCTCTCTCTGTCAT | [SEQ ID NO.: 5] |
| E19-1-R: | GTGAGATGGTGCCACATGCT | [SEQ ID NO.: 6] |
| E19-2-F: | GTCCATGGCTCTGAACCTCA | [SEQ ID NO.: 7] |
| E19-2-R: | CCACACAGCAAAGCAGAAAC | [SEQ ID NO.: 8] |
| E20-1-F: | CACACTGACGTGCCTCTCC | [SEQ ID NO.: 9] |
| E20-1-R: | CTTCGCATGGTGGCCAGA | [SEQ ID NO.: 10] |
| E20-2-1F: | CCTCCCCGTATCTCCCT | [SEQ ID NO.: 11] |
| E20-2-1R: | GGAGATAAGGAGCCAGGAT | [SEQ ID NO.: 12] |
| E21-1-F: | AGCAGGGTCTTCTCTGTTTCA | [SEQ ID NO.: 13] |
| E21-1-R: | GAGGGACAGATCATCATGGG | [SEQ ID NO.: 14] |
| E21-2-F: | TTTCCTGACACCAGGGACC | [SEQ ID NO.: 15] |
| E21-2-R: | TGACCTAAAGCCACCTCCTT. | [SEQ ID NO.: 16] |

Further, the cyclization is a splint mediated single strand DNA cyclization.

Further, the high throughput sequencing technologies are selected from Roche/454 FLX, Illumina/Hiseq/Miseq, Applied Biosystems SOLID and life Technologies/Ion Torrent/Proton. Illumina technology is used in the present invention.

According to another specific embodiment of the present invention, it provides a kit for non-invasively detecting EGFR gene mutations, comprising: reagents for extracting plasma DNAs, a DNA cyclase, primers and reagents for amplifying target DNAs. Conventional reagents or commercially available kits can be used in the extraction of plasma DNAs. Further, the amplification primers of the regions to be tested in the EGFR genes are a pair of primers that are adjacent and backward extended. Further, primers of the backward extended primer pair are located on 5' or 3' end of the sites or regions to be tested in the EGFR genes. Further, space of the backward extended primer pair is 0-½ of total base pairs of the plasma DNAs. Further, the backward extended primers aim at exon 18, exon 19, exon 20, or exon 21 of the EGFR genes. Further, the backward extended primers aim at exon 18, exon 19, exon 20, or exon 21 of the EGFR genes, and sequences of the primers are as follows:

| | | |
|---|---|---|
| E18-1-3F: | CCCAGCTTGTGGAGCCTC | [SEQ ID NO.: 1] |
| E18-1-3R: | GACAAGAACACAGAGACAAGGGT | [SEQ ID NO.: 2] |

-continued

| | | |
|---|---|---|
| E18-2-F: | GCAGGGCCTCTCATGGTC | [SEQ ID NO.: 3] |
| E18-2-R: | CCTGTGCCAGGGACCTTAC | [SEQ ID NO.: 4] |
| E19-1-F: | ACGTCTTCCTTCTCTCTCTGTCAT | [SEQ ID NO.: 5] |
| E19-1-R: | GTGAGATGGTGCCACATGCT | [SEQ ID NO.: 6] |
| E19-2-F: | GTCCATGGCTCTGAACCTCA | [SEQ ID NO.: 7] |
| E19-2-R: | CCACACAGCAAAGCAGAAAC | [SEQ ID NO.: 8] |
| E20-1-F: | CACACTGACGTGCCTCTCC | [SEQ ID NO.: 9] |
| E20-1-R: | CTTCGCATGGTGGCCAGA | [SEQ ID NO.: 10] |
| E20-2-1F: | CCTCCCCGTATCTCCCT | [SEQ ID NO.: 11] |
| E20-2-1R: | GGAGATAAGGAGCCAGGAT | [SEQ ID NO.: 12] |
| E21-1-F: | AGCAGGGTCTTCTCTGTTTCA | [SEQ ID NO.: 13] |
| E21-1-R: | GAGGGACAGATCATCATGGG | [SEQ ID NO.: 14] |
| E21-2-F: | TTTCCTGACACCAGGGACC | [SEQ ID NO.: 15] |
| E21-2-R: | TGACCTAAAGCCACCTCCTT. | [SEQ ID NO.: 16] |

Further, the kit comprises primers and reagents for pre-amplifying the regions to be tested in the EGFR genes. Specifically, the reagents and primers for pre-amplification include Taq DNA polymerase and its buffer, and primers for pre-amplification that are complementary to the Y-shape linkers.

Further, the kit comprises reagents for high throughput sequencing. Further, the reagents for high throughput sequencing are applicable to the following high throughput sequencing technologies: Roche/454 FLX, Illumina/Hiseq/Miseq, Applied Biosystems SOLID and life Technologies/Ion Torrent/Proton. Further, the plasma DNA connection linkers contain tagging sequences. Further, the plasma DNAs are pre-amplified before they are cyclised. Further, the cyclization is a splint mediated single strand DNA cyclization.

According to yet another specific embodiment of the present invention, it provides a use of primers according to EGFR gene exons in the preparation of diagnosing reagents or kits for non-invasively detecting EGFR gene mutations in subjects, characterized in that the diagnosing reagents or kits are applicable to a method for non-invasively detecting EGFR gene mutations in subjects comprising the following steps:
extracting plasma DNAs in subjects;
connecting the extracted plasma DNAs with tagging linkers;
PCR pre-amplifying the tagging linkers connected plasma DNAs;
cyclizing the amplified DNAs to obtain cyclised DNAs;
PCR amplifying the cyclised DNAs using the designed primers; and
high throughput sequencing the PCR amplified product and analyzing the EGFR gene mutations.

Further, the primers are a pair of primers that are adjacent and backward extended. Further, primers of the backward extended primer pair are located on 5' or 3' end of the EGFR gene exons. Further, space of the backward extended primer pair is 0-½ of total base pairs of the fragment DNAs. Further, the backward extended primers aim at exon 18, exon 19, exon 20, or exon 21 of the EGFR genes. Further, 5' end of the backward extended primers contains linker sequences for high throughput sequencing library. Further, the backward extended primers aim at exon 18, exon 19, exon 20, or exon 21 of the EGFR genes, and sequences of the primers are as follows:

| | | |
|---|---|---|
| E18-1-3F: | CCCAGCTTGTGGAGCCTC | [SEQ ID NO.: 1] |
| E18-1-3R: | GACAAGAACACAGAGACAAGGGT | [SEQ ID NO.: 2] |
| E18-2-F: | GCAGGGCCTCTCATGGTC | [SEQ ID NO.: 3] |
| E18-2-R: | CCTGTGCCAGGGACCTTAC | [SEQ ID NO.: 4] |
| E19-1-F: | ACGTCTTCCTTCTCTCTCTGTCAT | [SEQ ID NO.: 5] |
| E19-1-R: | GTGAGATGGTGCCACATGCT | [SEQ ID NO.: 6] |
| E19-2-F: | GTCCATGGCTCTGAACCTCA | [SEQ ID NO.: 7] |
| E19-2-R: | CCACACAGCAAAGCAGAAAC | [SEQ ID NO.: 8] |
| E20-1-F: | CACACTGACGTGCCTCTCC | [SEQ ID NO.: 9] |
| E20-1-R: | CTTCGCATGGTGGCCAGA | [SEQ ID NO.: 10] |
| E20-2-1F: | CCTCCCCGTATCTCCCT | [SEQ ID NO.: 11] |
| E20-2-1R: | GGAGATAAGGAGCCAGGAT | [SEQ ID NO.: 12] |
| E21-1-F: | AGCAGGGTCTTCTCTGTTTCA | [SEQ ID NO.: 13] |
| E21-1-R: | GAGGGACAGATCATCATGGG | [SEQ ID NO.: 14] |
| E21-2-F: | TTTCCTGACACCAGGGACC | [SEQ ID NO.: 15] |
| E21-2-R: | TGACCTAAAGCCACCTCCTT. | [SEQ ID NO.: 16] |

Further, the cyclization is a splint mediated single strand DNA cyclization. Further, the high throughput sequencing technologies are selected from Roche/454 FLX, Illumina/Hiseq/Miseq, Applied Biosystems SOLID and life Technologies/Ion Torrent/Proton.

EXAMPLES

Example 1

The plasma DNA template was amplified using self-designed linkers and according to a method for constructing a plasma DNA high throughput sequencing library (that is, PCR pre-amplification using phosphorylated primers after linker connection). The PCR product was purified by a gel cutting and cyclised by a splint connection. The cyclised product was digested by Exo III, purified, and screened by multiplex PCR with 8 pairs of back-to-back primers (the primers contain universal sequences for constructing a sequencing library). The mutation sites should be close to the forward primer or the reverse primer. The library was finally obtained by purifying the amplification product amplified by the universal primers.

1. Linker design. It is annealed to a double strand, wherein X is a tagging sequence:

ssCycADT-1:    GTCTCATCCCTGCGTGXXXXT ssCycADT-2:    pXXXXCACGCAGGGTACGTGT

The structure of connection product:

Top:
GTCTCATCCCTGCGTGXXXXTNNN AXXXXCACGCAGGGTACGTGT

Bottom:
TGTGCATGGGACGCACXXXXA  NNN TXXXXGTGCGTCCCTACTCTG

Primers:

ssCycUniprimer-F:    pGTCTCATCCCTGCGTG ssCycUniprimer-R:    pACACGTACCCTGCGTG

The library structure after pre-amplification:

pGTCTCATCCCTGCGTGXXXXTNNN AXXXXCACGCAGGGTACGTGT

CAGAGTAGGGACGCACXXXXA  NNN TXXXXGTGCGTCCCATGCACAp

Back-to-Back Primers for Amplification in Target Zones:

EXON18 (123 bp) [SEQ ID NO.: 17]

CAAGTGCCGTGTCCTGGCACCCAAGCCCATGCCGTGGCTGCTGGTCCCCCTGCTGGGCCATGTCTGGCACTGCTTTCCAGCATGGTG

AGGGCTGAGGTGACCCTTGTCTCTGTGTTCTTGTCCCCCCCAGCTTGTGGAGCCTCTTACACCCAGTGGAGAAGCTCCCAACCAAGC

TCTCTTGAGGATCTTGAAGGAAACTGAATTCAAAAAGATCAAAGTGCTGGGCTCCGGTGCGTTCGGCACGGTGTATAAGGTAAGGTC

CCTGGCACAGGCCTCTGGGCTGGGCCGCAGGGCCTCTCATGGTCTGGTGGGGAGCCCAGAGTCCTTGCAAGCTGTATATTTCCATCA

TCTACTTTACTCTTTGTTTCACTGAGTGTTTGG.

E18-1-3F: CCCAGCTTGTGGAGCCTC [SEQ ID NO.: 1]

E18-1-3R: GACAAGAACACAGAGACAAGGGT [SEQ ID NO.: 2]

E18-2-F: GCAGGGCCTCTCATGGTC [SEQ ID NO.: 3]

E18-2-R: CCTGTGCCAGGGACCTTAC [SEQ ID NO.: 4]

EXON19 (99 bp) [SEQ ID NO.: 18]

GCAATATCAGCCTTAGGTGCGGCTCCACAGCCCCAGTGTCCCTCACCTTCGGGGTGCATCGCTGGTAACATCCACCCAGATCACTGG

GCAGCATGTGGCACCATCTCACAATTGCCAGTTAACGTCTTCCTTCTCTCTCTGTCATAGGGACTCTGGATCCCAGAAGGTGAGAAA

GTTAAAATTCCCGTCGCTATCAAGGAATTAAGAGAAGCAACATCTCCGAAAGCCAACAAGGAAATCCTCGATGTGAGTTTCTGCTTT

GCTGTGTGGGGGTCCATGGCTCTGAACCTCAGGCCCACCTTTTCTCATGTCTGGCAGCTGCTCTGCTCTAGACCCTGCTCATCTCCA

CATCCTAAATGTTCACTTTCTATG.

E19-1-F: ACGTCTTCCTTCTCTCTCTGTCAT [SEQ ID NO.: 5]

E19-1-R: GTGAGATGGTGCCACATGCT [SEQ ID NO.: 6]

E19-2-F: GTCCATGGCTCTGAACCTCA [SEQ ID NO.: 7]

E19-2-R: CCACACAGCAAAGCAGAAAC [SEQ ID NO.: 8]

EXON20 (186 bp) [SEQ ID NO.: 19]

CCATGAGTACGTATTTTGAAACTCAAGATCGCATTCATGCGTCTTCACCTGGAAGGGGTCCATGTGCCCCTCCTTCTGGCCACCATG

CGAAGCCACACTGACGTGCCTCTCCCTCCCTCCAGGAAGCCTACGTGATGGCCAGCGTGGACAACCCCCACGTGTGCCGCCTGCTGG

GCATCTGCCTCACCTCCACCGTGCAGCTCATCACGCAGCTCATGCCCTTCGGCTGCCTCCTGGACTATGTCCGGGAACACAAAGACA

ATATTGGCTCCCAGTACCTGCTCAACTGGTGTGTGCAGATCGCAAAGGTAATCAGGGAAGGGAGATACGGGAGGGGAGATAAGGAG

CCAGGATCCTCACATGCGGTCTGCGCTCCTGGGATAGCAAGAGTTTGCCATGGGGATATG.

E20-1-F: CACACTGACGTGCCTCTCC [SEQ ID NO.: 9]

E20-1-R: CTTCGCATGGTGGCAGA [SEQ ID NO.: 10]

E20-2-1F: CCTCCCCGTATCTCCCT [SEQ ID NO.: 11]

E20-2-1R: GGAGATAAGGAGCCAGGAT [SEQ ID NO.: 12]

EXON21 (156 bp) [SEQ ID NO.: 20]

CTAACGTTCGCCAGCCATAAGTCCTCGACGTGGAGAGGCTCAGAGCCTGGCATGAACATGACCCTGAATTCGGATGCAGAGCTTCTT

CCCATGATGATCTGTCCCTCACAGCAGGGTCTTCTCTGTTTCAGGGCATGAACTACTTGGAGGACCGTCGCTTGGTGCACCGCGACC

TGGCAGCCAGGAACGTACTGGTGAAAACACCGCAGCATGTCAAGATCACAGATTTTGGGCTGGCCAAACTGCTGGGTGCGGAAGAGA

AAGAATACCATGCAGAAGGAGGCAAAGTAAGGAGGTGGCTTTAGGTCAGCCAGCATTTTCCTGACACCAGGGACCAGGCTGCCTTCC

CACTAGCTGTATTGTTTAACACATGCAGGGGAGGATGCTCTCCAGACATTCTGGGTGAGCTCGCAGC.

E21-1-F: AGCAGGGTCTTCTCTGTTTCA [SEQ ID NO.: 13]

E21-1-R: GAGGGACAGATCATCATGGG [SEQ ID NO.: 14]

E21-2-F: TTTCCTGACACCAGGGACC [SEQ ID NO.: 15]

E21-2-R: TGACCTAAAGCCACCTCCTT [SEQ ID NO.: 16]

2. Plasma free DNAs were extracted from 2 mL plasma.
3. End-filling:
The reaction mixture was prepared as follows:

TABLE 1

| | |
|---|---|
| PlasmaDNA solution | 38.5 μl |
| T4 DNA phosphorylation buffer (10X) | 5 μl |
| 10 mM dNTP mixture | 2 μl |
| T4 DNApolymerase | 2 μl |
| T4 DNA phosphorylase | 2 μl |
| Klenow enzyme | 0.5 μl |
| SterileH$_2$O | 0 μl |
| Total volume | 50 μl |

The mixture was placed in a 20° C. warm bath for 30 min. The DNA sample was purified on a purification column and eluted by 42 μl sterile dH$_2$O or an elution buffer.

4. Adding poly-adenine tail on the 3' end of the DNA fragments:
The reaction mixture was prepared as follows:

TABLE 2

| | |
|---|---|
| End-filled DNA | 32 μl |
| Klenow reaction buffer (10X) | 5 μl |
| dATP solution | 10 μl |
| klenow ex-enzyme (lacking 3'-5' exonuclease activity) | 3 μl |
| SterileH$_2$O | 0 μl |
| Total volume | 50 μl |

The mixture was placed in a 37° C. warm bath for 30 min. The DNA sample was purified on a column and eluted by 25 μl sterile dH$_2$O or an elution buffer.

5. Connecting linkers to the DNA fragments
The reaction mixture was prepared as follows:

TABLE 3

| | |
|---|---|
| End-filled dA-tailed DNA | 33 μl |
| Reaction buffer for quick connection (5X) | 10 μl |
| 5 μm DNA linker | 2 μl |
| Quick T4 DNA ligase (NEB) | 5 μl |
| Total volume | 50 μl |

The mixture was placed in a 20° C. warm bath for 15 min. The DNA sample was purified on a Qiagen column and eluted by 25 μl sterile dH$_2$O or an elution buffer.

6. Enriching the linker-modified DNA fragments by PCR pre-amplification
The PCR reaction mixture was prepared as follows:

| | |
|---|---|
| Buffers EB | 14 uL |
| 10X Taq ligase buffer | 5 uL |
| Split Oligo (10 μM) | 4 uL |
| Pre-lib | 25 uL |
| Taq ligase | 2 uL |
| Total volume | 50 uL |

PCR programs:

| | | |
|---|---|---|
| 95° C. | 30 s | 30 cycles |
| 50° C. | 2 min | |
| 4° C. | stop | |

TABLE 4

| | |
|---|---|
| DNA | 12.5 μl |
| Phusion DNA polymerase (Phusion DNA polymerase mixture) | 25 μl |
| PCR primer mixture | 2 μl |
| Ultrapure water | 10.5 μl |
| Total volume | 50 μl |

Amplification using the following PCR programs:
a. 98° C. 30 s;
b. 18 cycles as follows:
98° C. 10 s, 65° C. 30 s, 72° C. 30 s;
c. 72° C. 5 min;
d. maintained at 4° C.

6. PCR product was analyzed by electrophoresis on 2% agarose gel, and the results were shown in FIG. 4. The gel with target band of 200 bp was cut and recycled using a Qiagen Kit (FIG. 4), and eluted by 20 μl elution buffer.

7. Cyclization
The cyclization system was prepared as follows (Table 5)

| | |
|---|---|
| DNA template | 12 ul |
| Circ Ligase II 10X reaction buffer | 2 ul |
| 50 mM MnCl$_2$ | 1 ul |
| 5M Betaine (optional): | 4 ul |
| Circ Ligase II ssDNA ligase (100 U) | 1 ul |
| Total volume | 20 ul |

Reaction conditions

| | |
|---|---|
| 60° C. | 1 h |
| 80° C. | 10 min |
| 4° C. | stop |

8. Enzyme digestion:
All the cyclization products were digested by Exo III, and the digestion system was

| | |
|---|---|
| 10 × NE buffer | 1.2 ul |
| ExoIII | 1 ul |
| Cyclization product | 10 ul |

The digestion system was placed in a PCR machine, and reacted for 30 min at 37° C.
The digested product was purified on a purification column and dissolved in 30 ul EB buffer. The concentration was measured by Qubit, and the results were as follows:

| Sample Number | Concentration |
|---|---|
| 2 | 4 ng/ul |
| 3 | 0.3 ng/ul |
| 4 | 2.33 ng/ul |
| 5 | 5.74 ng/ul |

Figure 3:
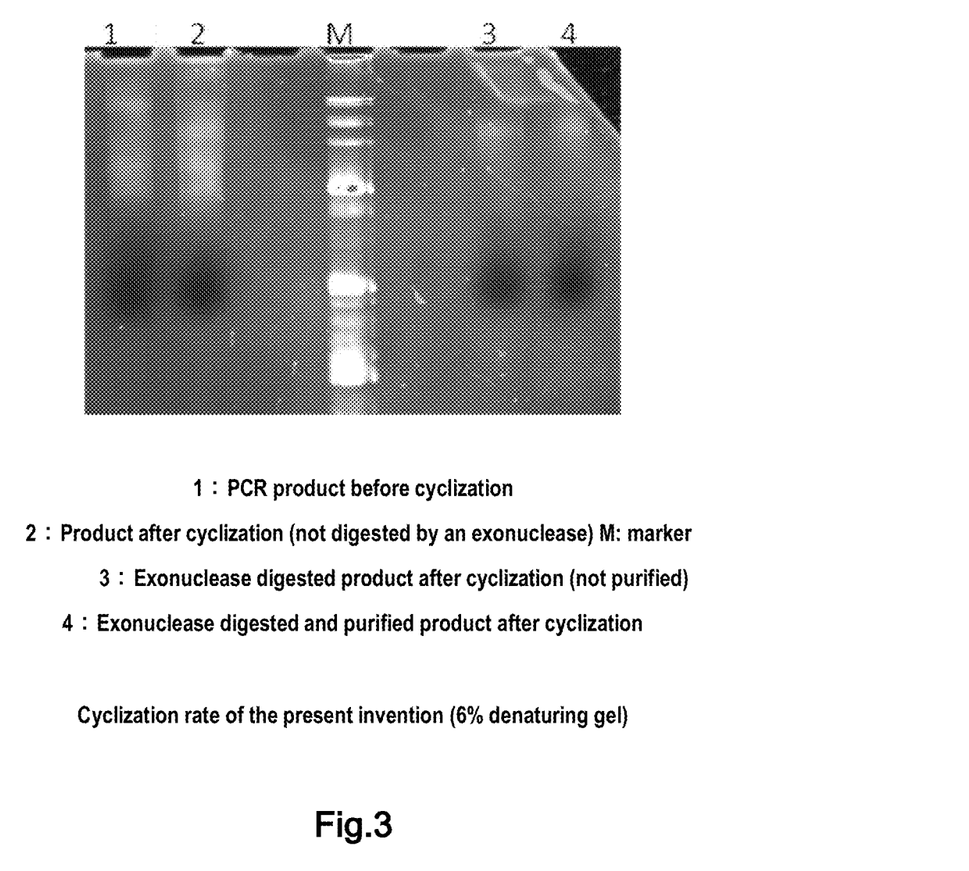

Examples of the present invention used a splint-mediated cyclization, which has a high rate of cyclization. Detailed tracking and detecting results of every step during the cyclization process were shown in FIG. 3. Lane 3 shows the cyclization product after digestion by exonuclease, which is the target product. The cyclization rate was about 20%.

9. Reverse PCR screening of the target zone using back-to-back primers

PCR reaction system was prepared as follows

TABLE 6

| dd H$_2$O | 13 or 18 ul |
|---|---|
| AmpliTaq Gold ® 360 Master Mix (2×) | 25 ul |
| CycEGFR18-F1 | 1 ul |
| CycEGFR18-R1 | 1 ul |
| DNA | 10 or 5 ul |
| Total volume | 50 ul |

Note:
the controls were P (with primers and without template) and N (template is un-cyclized ssCyc Lib)

PCR Reaction Conditions

TABLE 7

| 95° C. | 10 min | 1 cycle |
|---|---|---|
| 95° C. | 30 s | 30 cycles |
| 55° C. | 30 s | |
| 72° C. | 30 s | |
| 72° C. | 5 min | 1 cycle |

10. The second round PCR

The second round PCR was performed using products of the reverse PCR as templates. System

TABLE 8

| Phusion PCR Master Mix (2×) | 25 uL |
|---|---|
| P5-B1-F (10 mM) | 1 uL |
| Primer 2 -index 1-2 (10 uM) | 1 uL |
| Products of reverse PCR | 5 uL |
| ddH$_2$O | add to 50 uL |

Programs:

| 98° C. | 30 s | 1 cycle |
|---|---|---|
| 98° C. | 30 s | 12 cycles |
| 65° C. | 30 s | |
| 72° C. | 30 s | |
| 72° C. | 5 min | 1ycle |

Figure 4:
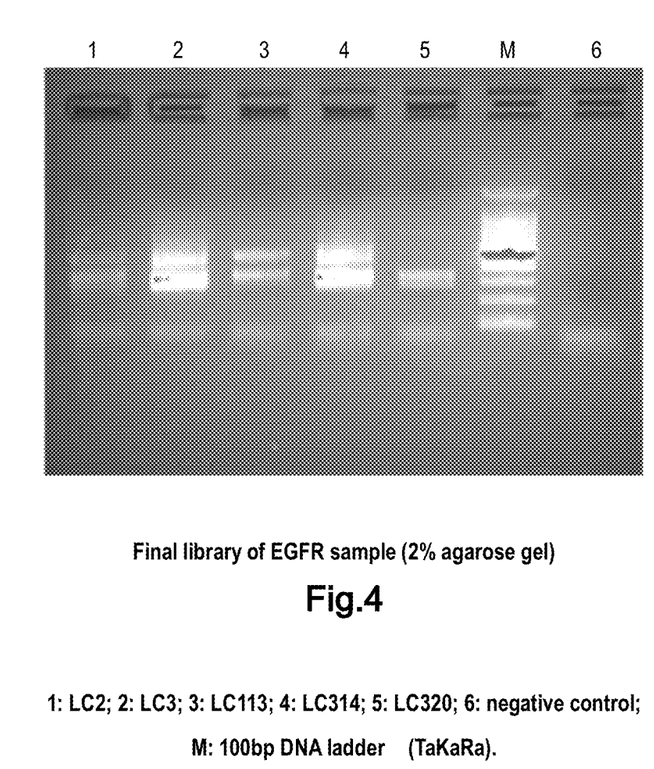
FIG. 4 shows the final EGFR sample library. This figure shows the results of 2% agarose gel. 1: LC2; 2: LC3; 3: LC113; 4: LC314; 5: LC320; 6: NTC (a negative control). The sample is a Lung Cancer (LC) sample.

10 uL PCR product from the second round PCR was analyzed by electrophoresis on 2% agarose gel, and the results were shown in FIG. 4.

11. The remaining 40 uL PCR product from the second round PCR was purified on a QIAGEN column, and dissolved in 20 uL EB buffer to generate the final library.

12. After quality control, the generated library was 250 bp double-end sequenced by IlluminaMiseq.

13. Every high throughput sequenced double-end sequences were assembled to one sequence based on repeated regions. Linkers were removed, and the sequence was restored to the original template sequence, which was then compared to the human genome (hg19). The unique template sequence set was counted by comparing the start and terminal coordinates and tagging sequences of the template sequence on the genome. Using the unique template sequence, genome coverage was then calculated, which can be used for evaluating the specificity of the library and calculating the somatic cell mutations in the EGFR region.

The results were compared with an EGFR gene mutation detection kit from AmoyDx (directed to the same cancer tissue) and a digital PCR. The comparison results were:

| Sample Number | ARMS Results (AmoyDx kit) | ddPCR Results (positive oil droplets/total oil droplets) | Sequencing Results (positive templates/total templates) |
|---|---|---|---|
| LC113 | 19-del | 19-del (2/723) | 19-del c.2239_2251>C (7/1192) |
| LC314 | WT | WT (del: 0/34; 1858r: 0/178; t790: 0/208) | WT (0/876) |
| LC320 | 19-del | 19-del (1/161) | 19-del c.2236_2250del15 (9/909) |
| LC2 | WT | n/a | WT (0/668) |
| LC3 | L858R | L858R (589/858) | c.2573T>G; p.L858R (1599/2510) |

5 samples tested by the method of the present invention showed highly consistent results with those tested by other methods. AMRS-PCR (amplification refractory mutation system) Taq DNA polymerase lacks 3'-5' exonuclease activity. Under certain conditions, effective amplification occurs only when the last base on 3' end of PCR primers is complementary to the template DNA. Mutated genes and wild type genes can be directly distinguished by PCR using suitable primers directed to different known mutations. This method is mainly for biopsy and FFPE samples. 5 mL peripheral blood before surgery and FFPE samples after surgery from the same patient were provided. The mutation type of FFPE samples on the known sites was detected by ARMS-PCR, and then plasma DNA was detected by digital PCR and the method of the present invention, respectively.

Example 2

Reliability of the present method was verified by detecting known cancer mutation sites. The method was the same as that disclosed in Example 1.

Cancer cell line DNA: cell DNAs containing hybrid c.2235_2249del15 (exon 19) mutation were broken by ultrasonication, 166±10 bp fragments were recycled and mixed with plasma DNAs from a normal person at certain ratio. The sensitivity and stability of the method were examined.

The detection results of c.2235_2249del15 were as follows:

| Sample Nos. | Prediction | Nos. of Total templates | Nos. of Non-Del templates | Nos. of Del templates | ratio |
|---|---|---|---|---|---|
| Sample 1 | 0% mutation | 862 | 862 | 0 | 0.00% |
| Sample 2 | 0.1 mutation | 438 | 433 | 5 | 1.09% |
| Sample 3 | 1% mutation | 905 | 843 | 62 | 6.78% |
| Sample 4 | 5% mutation | 880 | 786 | 94 | 10.67% |
| Sample 5 | 25% mutation | 1631 | 1017 | 614 | 37.65% |

What is claimed is:

1. A method for non-invasively detecting an EGFR gene mutation in a subject, comprising the following steps:
designing a pair of forward and reverse primers that are adjacent and backward extended,
targeting an exon of the EGFR gene wherein the exon is selected from the group consisting of exon 18, exon 19, exon 20, or exon 21, wherein the forward and reverse primer pairs that target exon 18 are selected from a group consisting of
E18-1-3Forward: CCCAGCTTGTGGAGCCTC [SEQ ID NO.:1];
E18-1-3Reverse: GACAAGAACACAGAGACAAGGGT [SEQ ID NO.:2] and
E18-2-Forward: GCAGGGCCTCTCATGGTC [SEQ ID NO.:3];
E18-2-Reverse: CCTGTGCCAGGGACCTTAC [SEQ ID NO.:4],
wherein the forward and reverse primer pairs that target exon 19 are selected from a group consisting of
E19-1-Forward: ACGTCTTCCTTCTCTCTGTCAT [SEQ ID NO.:5];
E19-1-Reverse: GTGAGATGGTGCCACATGCT [SEQ ID NO.:6] and
E19-2-Forward: GTCCATGGCTCTGAACCTCA [SEQ ID NO.:7];
E19-2-Reverse: CCACACAGCAAAGCAGAAAC [SEQ ID NO.:8],
wherein the forward and reverse primers that target exon 20 are
E20-2-1 Forward: CCTCCCCGTATCTCCCT [SEQ ID NO.:11];
E20-2-1 Reverse: GGAGATAAGGAGCCAGGAT [SEQ ID NO.:12], or
wherein the forward and reverse primer pairs that target exon 21 are selected from a group consisting of
E21-1-Forward: AGCAGGGTCTTCTCTGTTTCA [SEQ ID NO.:13];
E21-1-Reverse: GAGGGACAGATCATCATGGG [SEQ ID NO.:14] and
E21-2-Forward: TTTCCTGACACCAGGGACC [SEQ ID NO.:15];
E21-2-Reverse: TGACCTAAAGCCACCTCCTT [SEQ ID NO.:16];
extracting plasma DNAs from the subject;
connecting the extracted plasma DNAs with tagging linkers;
PCR pre-amplifying the tagging linkers connected plasma DNAs;
cyclizing the pre-amplified DNAs to obtain cyclized DNAs, wherein the cyclization is a splint mediated single strand DNA cyclization;
PCR amplifying the cyclized DNAs using the designed primers; and
high throughput sequencing the PCR amplified product and analyzing the EGFR gene mutations.

2. The method according to claim 1, characterized in that primers of the backward extended primer pair are located on 5' or 3' end of the EGFR gene exons.

3. The method according to claim 2, characterized in that 5' end of the backward extended primers contains linker sequences for high throughput sequencing library.

4. The method according to claim 1, characterized in that the EGFR genes in plasma DNAs have insertion, deletion, substitution or gene fusion mutations.

* * * * *

SEQUENCE LISTING

<160> NUMBER OF SEQ ID NOS: 20

<210> SEQ ID NO 1
<211> LENGTH: 18
<212> TYPE: DNA
<213> ORGANISM: Artificial
<220> FEATURE:
<223> OTHER INFORMATION: synthesized

<400> SEQUENCE: 1
cccagcttgt ggagcctc                                                     18

<210> SEQ ID NO 2
<211> LENGTH: 23
<212> TYPE: DNA
<213> ORGANISM: Artificial
<220> FEATURE:
<223> OTHER INFORMATION: synthesized

<400> SEQUENCE: 2
gacaagaaca cagagacaag ggt                                               23

<210> SEQ ID NO 3
<211> LENGTH: 18
<212> TYPE: DNA
<213> ORGANISM: Artificial
<220> FEATURE:
<223> OTHER INFORMATION: synthesized

<400> SEQUENCE: 3
gcagggcctc tcatggtc                                                     18

<210> SEQ ID NO 4
<211> LENGTH: 19
<212> TYPE: DNA
<213> ORGANISM: Artificial
<220> FEATURE:
<223> OTHER INFORMATION: synthesized

<400> SEQUENCE: 4
cctgtgccag ggaccttac                                                    19

<210> SEQ ID NO 5
<211> LENGTH: 24
<212> TYPE: DNA
<213> ORGANISM: Artificial
<220> FEATURE:
<223> OTHER INFORMATION: synthesized

<400> SEQUENCE: 5
acgtcttcct tctctctctg tcat                                              24

<210> SEQ ID NO 6
<211> LENGTH: 20
<212> TYPE: DNA
<213> ORGANISM: Artificial
<220> FEATURE:
<223> OTHER INFORMATION: synthesized

<400> SEQUENCE: 6
gtgagatggt gccacatgct                                                   20

<210> SEQ ID NO 7
<211> LENGTH: 20
<212> TYPE: DNA
<213> ORGANISM: Artificial

```
<220> FEATURE:
<223> OTHER INFORMATION: synthesized

<400> SEQUENCE: 7
gtccatggct ctgaacctca                                          20

<210> SEQ ID NO 8
<211> LENGTH: 20
<212> TYPE: DNA
<213> ORGANISM: Artificial
<220> FEATURE:
<223> OTHER INFORMATION: synthesized

<400> SEQUENCE: 8
ccacacagca aagcagaaac                                          20

<210> SEQ ID NO 9
<211> LENGTH: 19
<212> TYPE: DNA
<213> ORGANISM: Artificial
<220> FEATURE:
<223> OTHER INFORMATION: synthesized

<400> SEQUENCE: 9
cacactgacg tgcctctcc                                           19

<210> SEQ ID NO 10
<211> LENGTH: 18
<212> TYPE: DNA
<213> ORGANISM: Artificial
<220> FEATURE:
<223> OTHER INFORMATION: synthesized

<400> SEQUENCE: 10
cttcgcatgg tggccaga                                            18

<210> SEQ ID NO 11
<211> LENGTH: 17
<212> TYPE: DNA
<213> ORGANISM: Artificial
<220> FEATURE:
<223> OTHER INFORMATION: synthesized

<400> SEQUENCE: 11
cctccccgta tctccct                                             17

<210> SEQ ID NO 12
<211> LENGTH: 19
<212> TYPE: DNA
<213> ORGANISM: Artificial
<220> FEATURE:
<223> OTHER INFORMATION: synthesized

<400> SEQUENCE: 12
ggagataagg agccaggat                                           19

<210> SEQ ID NO 13
<211> LENGTH: 21
<212> TYPE: DNA
<213> ORGANISM: Artificial
<220> FEATURE:
<223> OTHER INFORMATION: synthesized

<400> SEQUENCE: 13
agcagggtct tctctgtttc a                                        21
```

<210> SEQ ID NO 14
<211> LENGTH: 20
<212> TYPE: DNA
<213> ORGANISM: Artificial
<220> FEATURE:
<223> OTHER INFORMATION: synthesized

<400> SEQUENCE: 14
gagggacaga tcatcatggg                                               20

<210> SEQ ID NO 15
<211> LENGTH: 19
<212> TYPE: DNA
<213> ORGANISM: Artificial
<220> FEATURE:
<223> OTHER INFORMATION: synthesized

<400> SEQUENCE: 15
tttcctgaca ccagggacc                                                19

<210> SEQ ID NO 16
<211> LENGTH: 20
<212> TYPE: DNA
<213> ORGANISM: Artificial
<220> FEATURE:
<223> OTHER INFORMATION: synthesized

<400> SEQUENCE: 16
tgacctaaag ccacctcctt                                               20

<210> SEQ ID NO 17
<211> LENGTH: 381
<212> TYPE: DNA
<213> ORGANISM: Homo sapiens

<400> SEQUENCE: 17
caagtgccgt gtcctggcac ccaagcccat gccgtggctg ctggtccccc tgctgggcca    60
tgtctggcac tgcttccag catggtgagg gctgaggtga cccttgtctc tgtgttcttg    120
tccccccag cttgtggagc ctcttacacc cagtggagaa gctcccaacc aagctctctt    180
gaggatcttg aaggaaactg aattcaaaaa gatcaaagtg ctgggctccg gtgcgttcgg    240
cacggtgtat aaggtaaggt ccctggcaca ggcctctggg ctgggccgca gggcctctca    300
tggtctggtg gggagcccag agtccttgca agctgtatat ttccatcatc tactttactc    360
tttgtttcac tgagtgtttg g                                             381

<210> SEQ ID NO 18
<211> LENGTH: 372
<212> TYPE: DNA
<213> ORGANISM: Homo sapiens

<400> SEQUENCE: 18
gcaatatcag ccttaggtgc ggctccacag ccccagtgtc cctcaccttc ggggtgcatc    60
gctggtaaca tccacccaga tcactgggca gcatgtggca ccatctcaca attgccagtt    120
aacgtcttcc ttctctctct gtcataggga ctctggatcc cagaaggtga gaaagttaaa    180
attcccgtcg ctatcaagga attaagagaa gcaacatctc cgaaagccaa caaggaaatc    240
ctcgatgtga gttctgctt tgctgtgtgg gggtccatgg ctctgaacct caggcccacc    300
ttttctcatg tctggcagct gctctgctct agaccctgct catctccaca tcctaaatgt    360
tcactttcta tg                                                        372

```
<210> SEQ ID NO 19
<211> LENGTH: 408
<212> TYPE: DNA
<213> ORGANISM: Homo sapiens

<400> SEQUENCE: 19
ccatgagtac gtattttgaa actcaagatc gcattcatgc gtcttcacct ggaaggggtc      60
catgtgcccc tccttctggc caccatgcga agccacactg acgtgcctct ccctccctcc     120
aggaagccta cgtgatggcc agcgtggaca accccacgt gtgccgcctg ctgggcatct     180
gcctcacctc caccgtgcag ctcatcacgc agctcatgcc cttcggctgc ctcctggact    240
atgtccggga acacaaagac aatattggct cccagtacct gctcaactgg tgtgtgcaga    300
tcgcaaaggt aatcagggaa gggagatacg gggaggggag ataaggagcc aggatcctca    360
catgcggtct gcgctcctgg gatagcaaga gtttgccatg gggatatg                  408

<210> SEQ ID NO 20
<211> LENGTH: 415
<212> TYPE: DNA
<213> ORGANISM: Homo sapiens

<400> SEQUENCE: 20
ctaacgttcg ccagccataa gtcctcgacg tggagaggct cagagcctgg catgaacatg     60
accctgaatt cggatgcaga gcttcttccc atgatgatct gtccctcaca gcagggtctt    120
ctctgtttca gggcatgaac tacttggagg accgtcgctt ggtgcaccgc gacctggcag    180
ccaggaacgt actggtgaaa acaccgcagc atgtcaagat cacagatttt gggctggcca    240
aactgctggg tgcggaagag aaagaatacc atgcagaagg aggcaaagta aggaggtggc    300
tttaggtcag ccagcatttt cctgacacca gggaccaggc tgccttccca ctagctgtat    360
tgtttaacac atgcagggga ggatgctctc cagacattct gggtgagctc gcagc          415
```